(12) United States Patent
Phipps

(10) Patent No.: US 9,592,128 B2
(45) Date of Patent: Mar. 14, 2017

(54) GLENOID IMPLANT

(71) Applicant: Zimmer, Inc., Warsaw, IN (US)

(72) Inventor: James P. Phipps, Pacifica, CA (US)

(73) Assignee: Zimmer, Inc., Warsaw, IN (US)

(*) Notice: Subject to any disclaimer, the term of this patent is extended or adjusted under 35 U.S.C. 154(b) by 0 days.

(21) Appl. No.: 14/732,841

(22) Filed: Jun. 8, 2015

(65) Prior Publication Data

US 2015/0272742 A1 Oct. 1, 2015

Related U.S. Application Data

(62) Division of application No. 13/865,695, filed on Apr. 18, 2013, now Pat. No. 9,066,806.

(60) Provisional application No. 61/637,089, filed on Apr. 23, 2012, provisional application No. 61/704,120, filed on Sep. 21, 2012.

(51) Int. Cl.
*A61F 2/40* (2006.01)
*A61B 17/86* (2006.01)
*A61F 2/30* (2006.01)
*A61F 2/46* (2006.01)

(52) U.S. Cl.
CPC ............ *A61F 2/4081* (2013.01); *A61B 17/86* (2013.01); *A61F 2002/3092* (2013.01); *A61F 2002/30125* (2013.01); *A61F 2002/30332* (2013.01); *A61F 2002/30405* (2013.01); *A61F 2002/30474* (2013.01); *A61F 2002/30614* (2013.01); *A61F 2002/30616* (2013.01); *A61F 2002/30878* (2013.01); *A61F 2002/4085* (2013.01); *A61F 2002/4641* (2013.01); *A61F 2230/0095* (2013.01); *A61F 2240/00* (2013.01)

(58) Field of Classification Search
CPC ................................ A61F 2/40; A61F 2/4081
See application file for complete search history.

(56) References Cited

U.S. PATENT DOCUMENTS

| 5,282,861 A | 2/1994 | Kaplan |
| 7,169,184 B2 | 1/2007 | Dalla Pria |
| 7,854,768 B2 | 12/2010 | Wiley et al. |
| 7,959,680 B2 | 6/2011 | Stone et al. |
| 8,906,103 B2* | 12/2014 | Stone ............... A61F 2/4014 623/19.11 |

(Continued)

FOREIGN PATENT DOCUMENTS

| EP | 1656910 A1 | 5/2006 |
| EP | 1787603 A1 | 5/2007 |

(Continued)

OTHER PUBLICATIONS

"U.S. Appl. No. 13/865,695, Non Final Office Action mailed Nov. 18, 2014", 8 pgs.

(Continued)

*Primary Examiner* — Jason-Dennis Stewart
(74) *Attorney, Agent, or Firm* — Schwegman Lundberg & Woessner, P.A.

(57) ABSTRACT

An apparatus can include a base plate. A glenosphere can be configured to be mountable to the base plate. The glenosphere can be adapted to operate with a complementary humeral component. The base plate can include a removable taper member on a side of the base plate facing the glenosphere. The taper member can be configured to mount the glenosphere to the base plate.

18 Claims, 6 Drawing Sheets

(56) References Cited

U.S. PATENT DOCUMENTS

| | | | |
|---|---|---|---|
| 9,066,806 | B2 | 6/2015 | Phipps et al. |
| 2004/0220673 | A1 | 11/2004 | Pria |
| 2012/0029647 | A1 | 2/2012 | Winslow et al. |
| 2012/0209392 | A1* | 8/2012 | Angibaud ............. A61F 2/4014 623/19.11 |
| 2013/0123929 | A1 | 5/2013 | Mcdaniel et al. |
| 2013/0150973 | A1* | 6/2013 | Splieth .................. A61F 2/4081 623/19.11 |
| 2013/0282129 | A1 | 10/2013 | Phipps |

FOREIGN PATENT DOCUMENTS

| | | |
|---|---|---|
| FR | 2737107 A1 | 1/1997 |
| FR | 2890853 A1 | 3/2007 |
| WO | WO-2013162999 A1 | 10/2013 |

OTHER PUBLICATIONS

"U.S. Appl. No. 13/865,695, Notice of Allowance mailed Mar. 2, 2015", 8 pgs.

"U.S. Appl. No. 13/865,695, Response filed Feb. 17, 2015 to Non-Final Office Action mailed Nov. 18, 2014", 8 pgs.

"U.S. Appl. No. 13/865,695, Response filed Nov. 10, 2014 to Restriction Requirement mailed Sep. 11, 2014", 5 pgs.

"U.S. Appl. No. 13/865,695, Restriction Requirement mailed Sep. 11, 2014", 6 pgs.

"International Application Serial No. PCT/US2013/037167, International Preliminary Report on Patentability mailed Mar. 27, 2014", 6 pgs.

"International Application Serial No. PCT/US2013/037167, International Search Report mailed Jun. 12, 2013", 6 pgs.

"International Application Serial No. PCT/US2013/037167, Written Opinion mailed Jun. 12, 2013", 7 pgs.

"European Application Serial No. 13718999.9, Examination Notification Art. 94(3) mailed Jan. 21, 2016", 4 pgs.

"European Application Serial No. 13718999.9, Office Action mailed Jan. 23, 2015", 2 pgs.

"European Application Serial No. 13718999.9, Response filed May 31, 2016 to Communication Pursuant to Article 94(3) EPC mailed Jan. 21, 2016", 21 pgs.

"European Application Serial No. 13718999.9, Response filed Aug. 3, 2015 to Office Action mailed Jan. 23, 2015", 8 pgs.

* cited by examiner

GLENOID IMPLANT

CLAIM OF PRIORITY

This application is a divisional of U.S. application Ser. No. 13/865,695, filed Apr. 13, 2013, which claims the benefit of U.S. Provisional Patent Application Ser. No. 61/637,089, filed on Apr. 23, 2012, and claims the benefit of U.S. Provisional Patent Application Ser. No. 61/704,120, filed on Sep. 21, 2012, the benefit of priority of each of which is claimed hereby, and each of which are incorporated by reference herein in its entirety.

FIELD

The present subject matter relates to an orthopedic system and specifically to a shoulder implant system.

BACKGROUND

In a healthy shoulder, the proximal humerus is generally ball-shaped, and articulates within a socket formed by the scapula, called the glenoid, to form the shoulder joint. Some implant systems for the total replacement of the shoulder joint generally replicate the natural anatomy of the shoulder. Such implant systems can include a humeral component having a stem that fits within the humeral canal, and an articulating head that articulates within the socket of a glenoid component implanted within the glenoid of the scapula.

Reverse-type shoulder implant systems have been developed in which the conventional ball-and-socket configuration that replicates the natural anatomy of the shoulder is reversed, such that a concave recessed articulating component is provided at the proximal end of the humeral component that articulates against a convex portion of a glenosphere of a glenoid component. For example, U.S. Pat. Nos. 7,854,768 and 7,959,680 discuss reverse shoulder systems.

OVERVIEW

A base plate and a glenosphere mountable to the base plate. The glenosphere can be sized or shaped or otherwise adapted to operate with a complementary humeral component. The base plate can include a removable taper member on a side of the base plate facing the glenosphere. The taper member can be configured to mount the glenosphere to the base plate.

The base plate can include an attachment section configured to allow attachment and removal of the removable taper section. The base plate can include a threaded rod to receive the removable taper member. The threaded rod can include an unthreaded lead-in section dimensioned to promote axial alignment of the taper member relative to the threaded rod. The base plate can be configured to receive screws to attach the base plate to a body. The base plate can include a first side configured to be attached to a body and a second side configured to be attached to the glenosphere. The taper member can include a 60 degree Morse taper region. The glenosphere can include a corresponding taper region to receive the taper member.

A base plate can be configured to be mounted to a body. The base plate can include a first side having a porous metallic surface that can be configured to be mounted to a glenoid and a second side that can have an attachment section. The base plate can include one or more holes, such as to respectively receive screws to attach the base plate to a body. A taper member can be removably attached to the attachment section of the base plate. A glenosphere can be mounted to the taper member. The glenosphere can be sized or shaped or otherwise adapted to operate with a complementary humeral component mounted to a stem.

The attachment section can include a threaded rod and the taper member can include a mating threaded hole. The threaded rod can include an unthreaded lead-in section, which can be dimensioned to promote axial alignment of the taper member relative to the threaded rod. The base plate can include an extended stem on the first side. The taper member can include a 60 degree Morse taper region. The glenosphere can include a corresponding taper region to receive the taper member.

A method can include attaching a removable taper member to a reverse shoulder system base plate, and mounting a glenosphere to the taper member.

Attaching can include threading the taper member to the reverse shoulder system base plate. Attaching can include placing the taper member over an unthreaded lead-in section of a threaded rod on the reverse shoulder base plate to axially align the taper member to the threaded rod before the threads of the threaded rod meet the threads of the taper member. The method can include removing the taper member and attaching a second, different taper member to the reverse shoulder system base plate. The taper member can include a 60 degree Morse taper region. The glenosphere can include a corresponding taper region to receive the taper member.

A base plate can have an oblong shape and include first and second stems extending from a first side of the base plate. The base plate can include a taper attachment section on a second side of the base plate. The base plate can be configured to be mounted to a glenoid. A removable taper member can be mounted to the taper attachment section, and a shoulder implant component can be mounted to the removable taper member.

The shoulder implant component can include a glenosphere. The shoulder system can include a humeral stem and an articulating liner attached to the humeral stem, the articulating liner can be adapted to articulate about the glenosphere. The shoulder implant component can include a glenoid component including a concave articulating glenoid surface. The shoulder system can include a humeral stem and a glenosphere attached to the humeral stem, the glenosphere can be shaped to articulate with the concave articulating glenoid surface. The removable taper member can be mounted to the base plate at a non-centered location of the base plate. The base plate can include a surface profile that includes one dimension greater than another dimension. The taper attachment section can include a threaded post and the first stem is aligned with the threaded post. The base plate can include three holes configured to receive screws to attach the base plate to a body. The attachment section can include a threaded rod configured to receive the removable taper member. The threaded rod can include an unthreaded lead-in section dimensioned to promote axial alignment of the taper member relative to the threaded rod.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

As used herein, the following directional definitions apply. Anterior and posterior mean nearer the front or nearer the rear of the body, respectively, proximal and distal mean nearer to or further from the root of a structure, respectively, and medial and lateral mean nearer the sagittal plane or further from the sagittal plane, respectively. The sagittal plane is an imaginary vertical plane through the middle of the body that divides the body into right and left halves.

Figure 1:
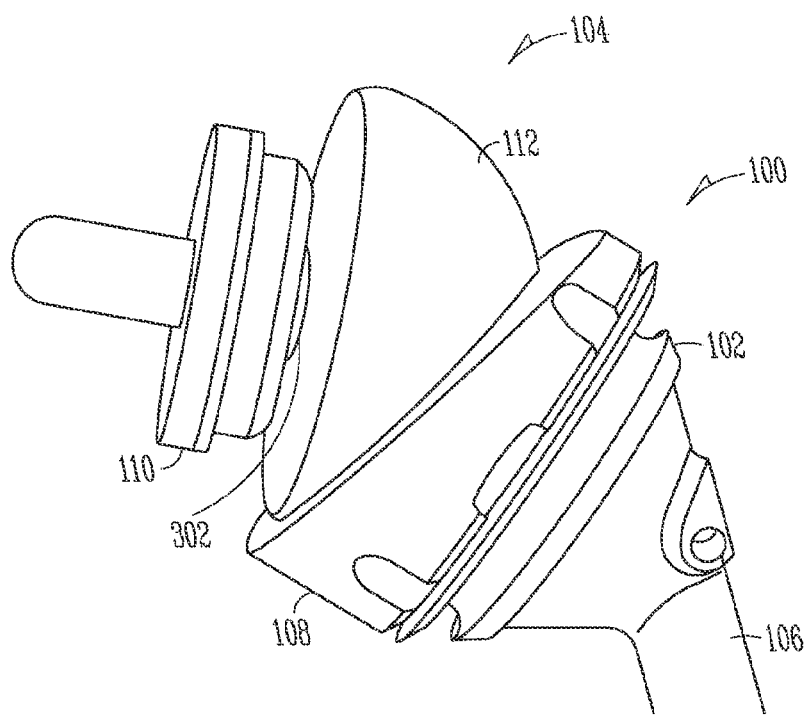
FIG. 1 shows an implant system for a reverse shoulder arthroplasty.

FIG. 1 shows an example of an implant system 100 for a reverse shoulder arthroplasty. The reverse shoulder implant system 100 can include a humeral component 102 that can be sized or shaped or otherwise adapted to be fitted within a prepared proximal end canal of a humerus, and a glenoid component 104 that can be sized or shaped or otherwise configured to be mounted to a prepared surface of a patient's glenoid, such as via a plurality of screws. The humeral component 102 can articulate about the glenoid component 104, such as to replicate the movement of the natural shoulder joint.

The humeral component 102 can include a humeral stem 106 and an articulating liner 108 that can be fitted to the humeral stem 106 and that can have a concave articulating surface. The glenoid component 104 can include a glenoid base plate 110, a removable taper member 302, and a glenosphere 112 that can be fitted to the taper member 302 of the glenoid base plate 110 and having a convex articulating surface. In use, the articulating liner 108 can articulate about the glenosphere 112.

Figure 2:
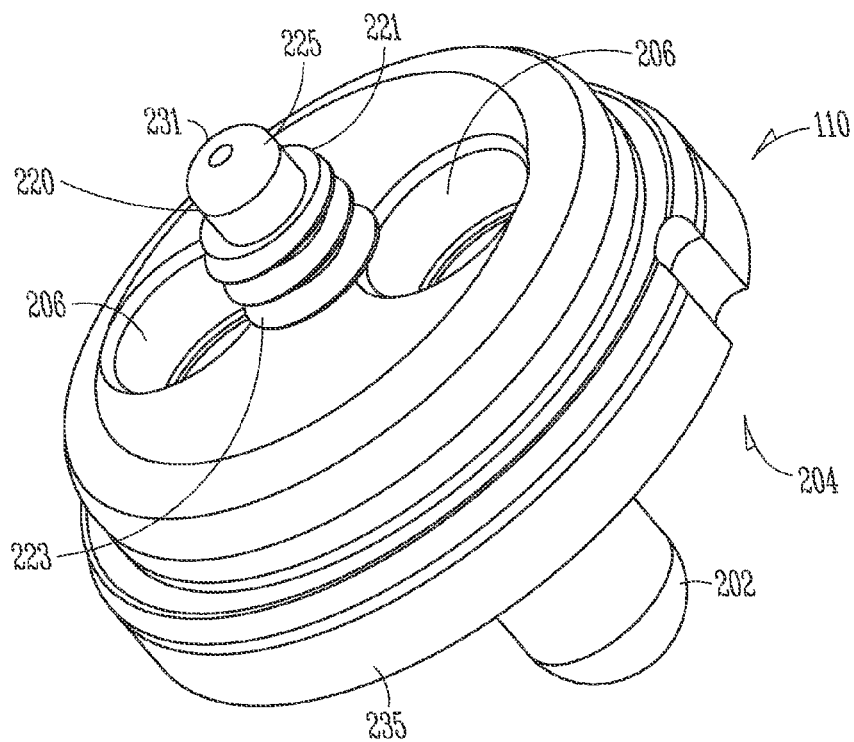
FIG. 2 shows a perspective view of a base plate for the reverse shoulder implant system of FIG. 1.

FIG. 2 shows a perspective view of an example of the base plate 110. The base plate 110 can be configured to be mounted to the glenoid of a patient and can include a stem 202 that can extend from a first side 204 of the base plate 110. An outer porous surface on the first side 204 can be adapted to promote bone growth. For example, the first side 204 can include a porous metallic surface 235. Two or more holes 206 can extend through the base plate 110 and can be configured to respectively accept attachment screws.

For example, the first side 204 can include a highly porous biomaterial useful as a bone substitute and/or cell and tissue receptive material. An example of such a material can be produced using Trabecular Metal® technology generally available from Zimmer, Inc., of Warsaw, Ind. Trabecular Metal® is a trademark of Zimmer Technology, Inc. Such a material can be formed from a reticulated vitreous carbon foam substrate, which can be infiltrated and coated with a biocompatible metal, such as tantalum, etc., such as using a chemical vapor deposition ("CVD") process, such as in the manner disclosed in detail in U.S. Pat. No. 5,282,861, the disclosure of which is incorporated herein by reference. One or more other metals such as niobium, titanium, or one or more alloys of tantalum and niobium with each other or with one or more other metals can also be used.

The base plate 110 can include a taper attachment section 220 that can extend from a second side of the base plate 110. The attachment section 220 can be adapted to receive the removal taper member 302 and to allow a user to remove the removable taper member 302 without damaging the base plate 110. The attachment section 220 can include a threaded rod 221 such as to receive the removable taper member. The threaded rod 221 can extend from the surface of the base plate 110 and can include a lower threaded section 223, a rounded top 231, and an unthreaded lead-in section 225. The unthreaded lead-in section 225 can have a height dimensioned to promote axial alignment of the removable taper member 302 relative to the threaded rod 221 when the taper member 302 is mounted to the base plate 110. The unthreaded lead-in section 225 and/or the rounded top 231 can help inhibit thread misalignment between the two members and can make it easier for a user to install the taper member to the threaded rod. The threaded rod 221 can include a ¼-20 threaded rod, such as can protrude from the center axis of the base plate 110.

Figure 3:
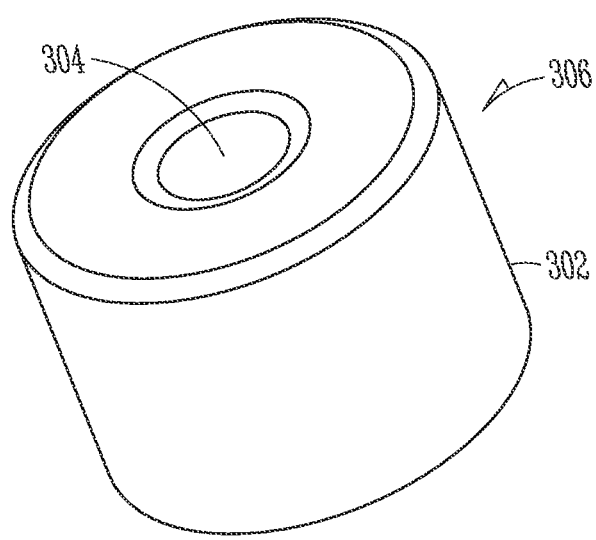
FIG. 3 shows a taper member.

FIG. 3 shows an example of the taper member 302. The taper member 302 can be generally cylindrical with a tapered outer surface shape 306. The taper member 302 can include a threaded hole 304 that can be configured to removably receive the threaded rod 221 such as discussed herein. This allows taper member 302 to be removed from the base plate 110 and a similar or different taper member can be mounted to the base plate 110 without the base plate 110 having to be removed from its implanted location. This removability/interchangeability of the present taper system allows a doctor to revise the taper region of the implant as needed without unnecessary complications. The taper member 302 can be configured to mount the glenosphere 112 to the base plate 110. The taper member 302 can have a 60 degree Morse taper region defined by its tapered outer surface shape 306. The Morse taper region can provide a conical press-fit fixation of the taper member 302 into the corresponding taper region of the glenosphere 112, such as for providing accurate alignment and frictional fixation. Another Morse taper size can be used depending on need and requirements of the corresponding glenosphere used.

Figure 4:
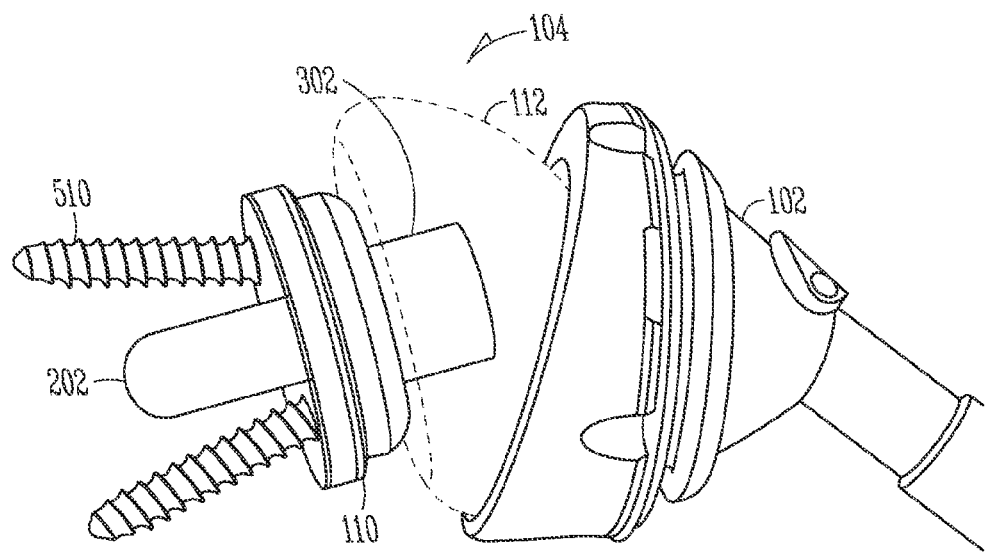
FIG. 4 shows a side view of the reverse shoulder implant system.
Figure 5:
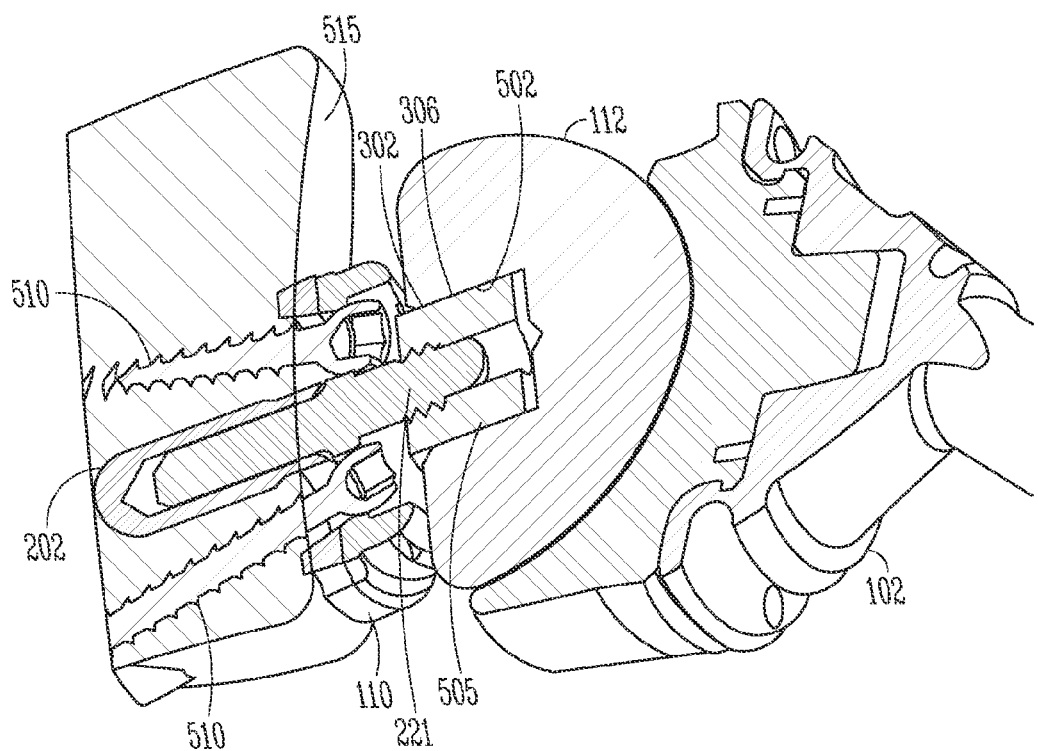
FIG. 5 shows a cross-section view of the reverse shoulder implant system.

FIG. 4 shows a side view of an example of the reverse shoulder implant system, and FIG. 5 shows a cross-section view of the example of the reverse shoulder implant system.

The system can include the humeral component 102 fitted to a glenoid component 104 that can include the glenosphere 112. The base plate 110 can be mounted to a prepared surface of a patient's glenoid 515, such as via a plurality of screws 510. The removable taper member 302 can be fitted to the glenosphere 112. The glenosphere 112 can have a female taper region 502 that can form a cavity 505 and the removable taper member 302 can fit within the corresponding taper region 502.

The base plate stem 202 can extend from the base plate 110 and can be implanted within the glenoid area. The threaded rod 221 can extend from the surface of the base plate 110 and can receive the removable taper member 302.

In use, the base plate 110 can be implanted to the patient's glenoid 515. After the attachment screws 510 have been attached, the taper member 302 can be screwed onto the base plate 110 over the threaded rod 221. The glenosphere 112 can then be force fit over the taper member 302. If revision is needed, the glenosphere 112 can be removed from the taper member 302 and, if needed, the taper member 302 can be removed, such as by unthreading from the base plate 110. A similar or a different taper member can then be threaded onto the threaded rod 221. For example, if the doctor decides to use a different size glenosphere having a different size taper region 502, a matching taper member can be used. Depending on the glenosphere used, or for other considerations, the different sized taper member can be any combination of wider, thinner, taller, or shorter than the present taper member.

Accordingly, the present system can include a glenoid component 104 with a removable/interchangeable taper member 302 such as to allow for the removal of the taper member 302 of the implant without disrupting the rest of the implant that has established bone ingrowth. For example, sometimes during a revision surgery, the entire glenoid component from a total shoulder arthroplasty procedure must be removed to provide an undisturbed taper surface for the implant. In the present system, taper member 302 can be exchanged for a different type of taper for use with a different glenoid head to be installed in the patient. For example, humeral heads, usually intended for a standard shoulder procedure, can be used as glenospheres when using the present system. This system can also allow a surgeon to choose more options for particular anatomic situations, such as where spacing is required from the glenoid component, which is believed not possible with current systems on the market.

This system can allow for the use of the readily available humeral heads for this proposed system. The removable taper member 302 can allow a surgeon to replace only the tapered section of the glenoid implant, such as if this were to become compromised by a failed attempt to seat the glenosphere during the surgery. The removable taper member 302 can also be helpful to a surgeon performing a revision procedure because the doctor would be able to insert a fresh taper component without disturbing the rest of the implant, which may have already established bone ingrowth.

Moreover, using a removable taper member 302 can allow for a shorter or taller taper member to used, which can allow the doctor to control the axial distance of the glenoid component 104. Having an axial distance adjustable glenoid component 104 can allow surgeons to custom build each implant to the particular patient anatomy with the already-existing adjustable humeral component for tightening the joint space. For example, a surgeon can choose a shorter or longer taper member 306, such as depending on the chosen humeral head, and the patient's anatomy, to provide the desired fit. Also, choosing a different height for the taper member 306 can provide the ability to tension the joint from the glenoid side of the shoulder. It is believed that this can help provide less scapular notching from the humeral component than is seen with current competitive systems on the market, since the humeral component 102 can be moved away from the scapula. It is also believed that the humeral heads currently offered (for normal shoulder work) are available in larger sizes, which are not presently common to reverse shoulder systems currently available. The present interchangeable taper member 306 would allow surgeons more adjustability in joint anatomy, which may lead into orthopedic avenues in total shoulder arthroplasty that have not yet been uncovered.

Figure 6:
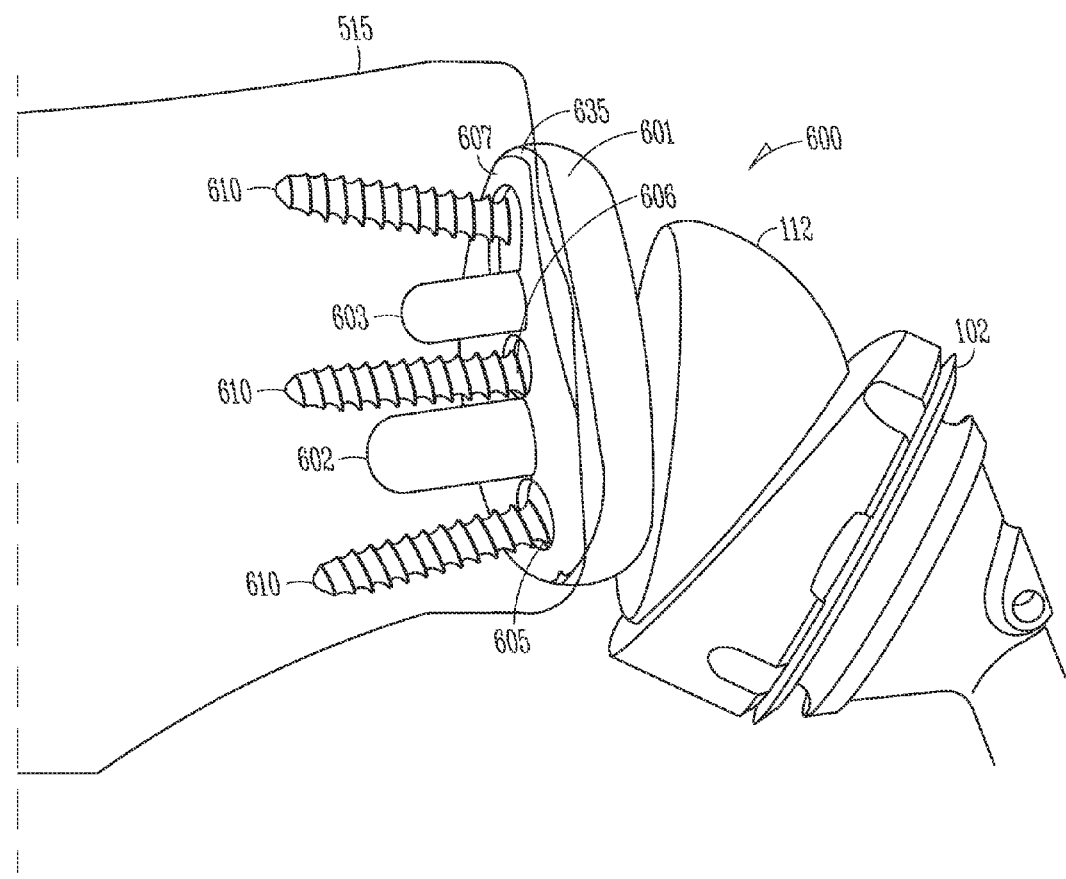
FIG. 6 shows a rear perspective view of a shoulder implant system.
Figure 7:
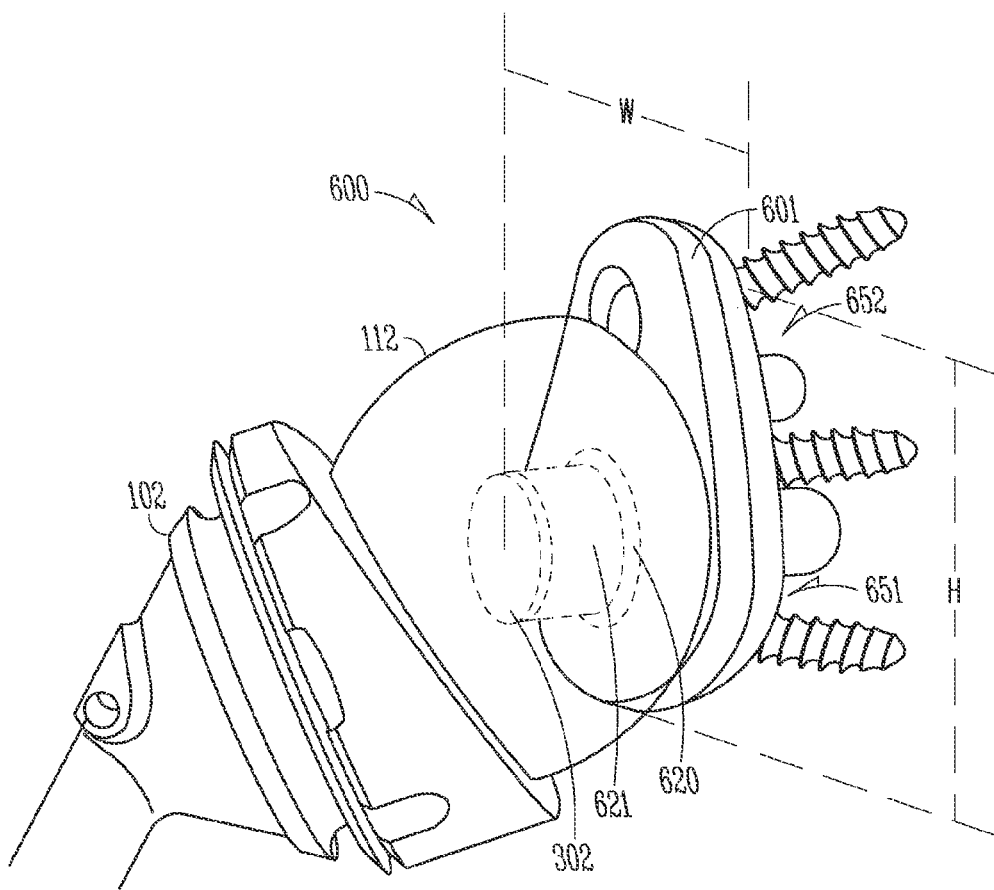
FIG. 7 shows a front perspective view of the shoulder implant system of FIG. 6.

FIG. 6 shows a rear perspective view of a shoulder implant system 600 and FIG. 7 shows a front perspective view of the shoulder implant system 600. Shoulder system 600 can include the humeral component 102 and a shoulder implant component, such as the glenosphere 112, as discussed above. Shoulder system 600 can also include a base plate 601.

The base plate 601 can be configured to be mounted to the glenoid 515 of a patient and can include a first, lower stem 602 that can extend from a first side of the base plate 601, and a second, upper stem 603 that can also extend from the first side of the base plate. The upper stem 603 can be shorter than the lower stem 602. An outer porous surface on the first side can be adapted to promote bone growth. For example, the first side can include a porous metallic surface, such as discussed above. Three holes 605, 606, and 607 can extend through the base plate 601 and can be configured to respectively accept attachment screws 610. The three screw holes 605, 606, and 607 are generally aligned with each other and with the lower and upper stems 602 and 603, with the lower screw located below lower the lower stem 602, the middle screw located between the lower stem 602 and the upper stem 603, and the upper screw located above the upper stem 603.

The base plate 601 can include a taper attachment section 620 that can extend from a second side of the base plate 601. The attachment section 620 is similar to the attachment section 220, discussed above. The attachment section 620 can be adapted to receive the removal taper member 302 and to allow a user to remove the removable taper member 302 without damaging the base plate 601. The attachment section 620 can include a threaded rod 621 such as to receive the removable taper member 302. The threaded rod 621 can extend from the surface of the base plate 601 and can include a lower threaded section, a rounded top, and an unthreaded lead-in section, as discussed above for threaded rod 221.

The base plate 601 can include an oblong, eccentric surface profile shape that is not symmetric. For example, the base plate 601 can include an oblong surface profile that includes one dimension, such as height H, that is greater than a second dimension, such as width W. The base plate 601 includes a first, lower section 651 having a generally round shape and a second, upper section 652 which extends from the lower section 651. In an example, the upper section 652 can be narrower than the lower section 651. The lower section 651 and the upper section 652 define an eccentric, oblong surface profile shape for the base plate 601. The base plate 601 can include at least a portion of upper section 652 that can extend above the mounted glenosphere 112 so that the surface profile shape is asymmetric relative to the glenosphere 112.

The removable taper 302 can be mounted to the base plate 601 at a non-centered location of the base plate 601. For example, the threaded post 621 can be centered relative to the lower section 651 and offset from upper section 652. The lower stem 602 can be located such that the lower stem 602 aligns with the threaded rod 620 and removable taper 302. Thus, lower stem 602 can provide the same primary support for the base plate as stem 202 described above. (FIG. 4). The upper section 652 of the oblong, eccentrically shaped base plate 601 provides room on base plate 601 for the upper screw 610 and the upper stem 603. This allows the base plate 601 to be mounted to the proximal bone that is often undisturbed by current shoulder systems.

The oblong, eccentric base plate 601 allows the base plate 601 to better overcome bending moments that are applied to the shoulder component mounted thereon. For example, in FIG. 6 forces applied to glenosphere 112 are transferred to the base plate 601. If due to anatomical or other reasons, the surgeon uses a longer removable taper 302, the bending moment of the glenosphere 112 on the base plate 601 will be greater. Thus, if the shoulder component, such as glenosphere 112 is lateralized, large bending moments may be applied to the glenoid bone stock, which can contribute to loss of bone ingrowth and implant loosening over time. The oblong, eccentric base plate 601 allows for the bending moment forces to be also resisted by the upper portion including upper post 603 and the upper screw 610.

In use, the base plate 601 can be implanted to the patient's glenoid 515. Before or after the attachment screws 610 have been attached, the taper member 302 can be screwed onto the base plate 610 over the threaded rod 621. The glenosphere 112 can then be force fit over the taper member 302. If revision is needed, the glenosphere 112 can be removed from the taper member 302 and, if needed, the taper member 302 can be removed, such as by unthreading from the base plate 601. A similar or a different taper member can then be threaded onto the threaded rod 621. For example, if the doctor decides to use a different size glenosphere having a different size taper region, a matching taper member can be used. Depending on the glenosphere used, or for other considerations, the different sized taper member can be any combination of wider, thinner, taller, or shorter than the present taper member.

Figure 8:
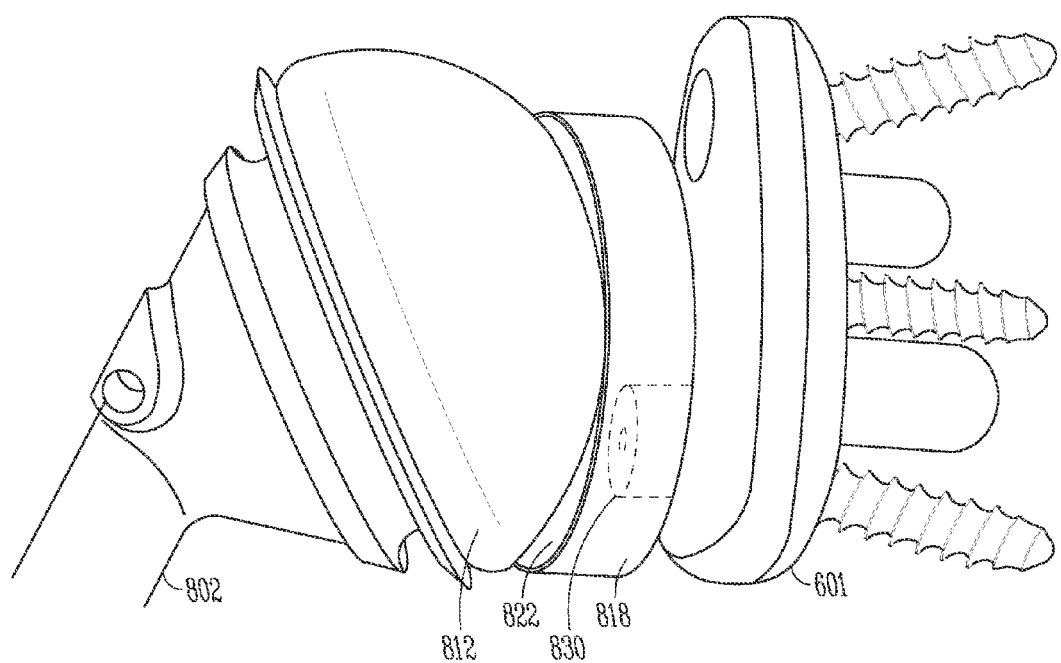
FIG. 8 shows a perspective view of a shoulder implant system.

FIG. 8 shows a shoulder implant system for a standard shoulder arthroplasty. The shoulder implant system can include a humeral stem 802 that can be sized or shaped or otherwise adapted to be fitted within a prepared proximal end canal of a humerus, a glenosphere 812 mounted to an end of the humeral stem 802, and a shoulder implant component, such as a glenoid component 818. The glenosphere 812 can include a convex articulating outer surface shaped to articulate with a complementary concave articulating glenoid surface 822 of the glenoid component 818, such as to replicate the movement of the natural shoulder joint.

The glenoid component 818 is mounted to the base plate 601 using a taper member 830, in a similar manner as the attachment of the glenosphere 112, discussed above. (FIG. 7).

Again, the oblong, eccentric shape of base plate 601 allows the base plate 601 to better overcome bending moments that are applied to the shoulder component, such as glenoid component 818, mounted thereon. For example, forces applied to glenosphere 812 are transferred to glenoid component 818 and then to the base plate 601. If due to anatomical or other reasons, the surgeon uses a longer removable taper 302, or a larger glenosphere 812, the bending moment of the on the base plate 601 will be greater. If large bending moments are applied to the glenoid bone stock, this can contribute to loss of bone in-growth and implant loosening over time. The oblong, eccentric base plate 601 allows for the bending moment forces to be also resisted by the upper portion including upper post and the upper screw being attached to the body.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The claimed invention is:

1. A method comprising:
attaching a removable taper member to a reverse shoulder system base plate, the base plate having an attachment post, wherein the removable taper member is configured to be mounted over the attachment post and un-mounted from the attachment post; and
mounting a glenosphere to the taper member.

2. The method of claim 1, wherein attaching includes threading the taper member to the reverse shoulder system base plate.

3. The method of claim 2, wherein attaching includes placing the taper member over an unthreaded lead-in section of the threaded attachment post on the reverse shoulder base plate to axially align the taper member to the threaded attachment post before the threads of the threaded attachment post meet the threads of the taper member.

4. The method of claim 1, further comprising removing the taper member and attaching a second, different taper member to the reverse shoulder system base plate.

5. The method of claim 4 wherein the second, different taper member has a different height than the taper member.

6. The method of claim 1, wherein the taper member includes a 60 degree Morse taper region.

7. The method of claim 6, wherein the base plate includes an oblong shape.

8. The method of claim 1 wherein the removable taper member is mounted to the base plate at a non-centered location of the base plate.

9. The method of claim 1 wherein the attachment post has a threaded section that corresponds to a threaded section of the taper member.

10. The method of claim 1 wherein no portion of the taper member contacts bone.

11. The method of claim 1 wherein no portion of the attachment post contacts bone.

12. The method of claim 1 wherein the attachment post attaches to a stem, the stem extending from an opposite side of the baseplate than the attachment post.

13. The method of claim 12 wherein the stem has a porous outer surface to promote bony in-growth.

14. The method of claim 1 further including removing the taper during a revision procedure in which at least a portion of a previously-implanted shoulder system is removed.

15. The method of claim 1 wherein the taper member is configured to mate with multiple sizes of glenospheres.

16. A method comprising:
    threading a removable taper member to a reverse shoulder system base plate, the base plate having an attachment post, wherein the removable taper member is configured to be mounted over the attachment post and un-mounted from the attachment post, wherein the attachment post has a threaded section that corresponds to a threaded section of the taper member; and
    mounting a glenosphere to the taper member.

17. The method of claim 16, wherein threading includes placing the taper member over an unthreaded lead-in section of the threaded attachment post on the reverse shoulder base plate to axially align the taper member to the threaded attachment post before the threads of the threaded attachment post meet the threads of the taper member.

18. The method of claim 16, wherein the removable taper member is mounted to the base plate at a non-centered location of the base plate.

* * * * *